(12) United States Patent
Weston et al.

(10) Patent No.: US 6,620,135 B1
(45) Date of Patent: Sep. 16, 2003

(54) NEEDLELESS INJECTORS

(75) Inventors: Terence Edward Weston, Eye (GB); Graham Roger Gibbins, Brundall (GB); Matthew Simon Nussey, Sheffield (GB)

(73) Assignee: Weston Medical Limited, Suffolk (GB)

( * ) Notice: Subject to any disclaimer, the term of this patent is extended or adjusted under 35 U.S.C. 154(b) by 0 days.

(21) Appl. No.: 09/763,399

(22) PCT Filed: Aug. 5, 1999

(86) PCT No.: PCT/GB99/02586
§ 371 (c)(1),
(2), (4) Date: Mar. 23, 2001

(87) PCT Pub. No.: WO00/10630
PCT Pub. Date: Mar. 2, 2000

(30) Foreign Application Priority Data

Aug. 19, 1998 (GB) ............................................. 9818110

(51) Int. Cl.[7] .............................................. A67M 37/00
(52) U.S. Cl. ............................ 604/140; 604/68; 604/69
(58) Field of Search ............................ 604/65, 66, 67, 604/68, 70, 69, 71, 44, 45, 140; 128/DIG. 12, DIG. 13

(56) References Cited

U.S. PATENT DOCUMENTS

| | | | | |
|---|---|---|---|---|
| 2,605,763 A | | 8/1952 | Smoot | 128/173 |
| 2,680,349 A | | 6/1954 | Sutermeister | 128/173 |
| 4,596,556 A | * | 6/1986 | Morrow et al. | 604/70 |
| 5,024,656 A | * | 6/1991 | Gasaway et al. | 604/70 |
| 5,520,639 A | * | 5/1996 | Peterson et al. | 604/68 |
| 6,096,002 A | * | 8/2000 | Landau | 604/68 |
| 6,135,979 A | | 10/2000 | Weston | 604/68 |

FOREIGN PATENT DOCUMENTS

WO    WO 95/03844    2/1995

* cited by examiner

*Primary Examiner*—Manuel Mendez
(74) *Attorney, Agent, or Firm*—Darby & Darby (57) ABSTRACT

A pressurised gas powered actuator comprising a piston (3) operating in a cylinder (1). The stroke of the piston (3) may be reduced by uncovering one or more holes (14, 20) in the cylinder wall to permit the escape of the pressurised gas at a predetermined position along the swept wall of the cylinder. Alternatively, the piston (401) may be connected to a rod (402) which has a gas vent (406) formed therein, the position of the rod (402) with respect to the piston (401) being variable to adjust the stroke of the piston (401).

10 Claims, 7 Drawing Sheets

NEEDLELESS INJECTORS

This invention relates to needleless injectors.

In International Patent Publication No. WO 95/03844, a needleless injector is disclosed. This is used to deliver liquid medicaments through a patient's skin by means of a high pressure jet of the medicament, generated by a piston pump. The energy for operating the pump may be derived from a coiled spring, pyrotechnic charge, hydraulic pressure, or pressurised gas.

Injectors are available using many different types of energy, and the energy may be supplied by the user, for example where a spring is manually compressed and latched to temporarily store the energy until it is required to "fire" the injector. Alternatively, the injector may be supplied having the energy already stored—for instance by means of a precompressed spring, or pyrotechnic charge.

Some injectors are intended for disposal after a single use, whereas others have a reoadable energy storage means and a disposable medicament cartridge, and there are many combinations to suit particular applications and markets. For the purposes of the present disclosure, the term "actuator" will be used to describe the energy storage and release mechanism, whether or not it is combined with the medicament cartridge. In all cases, it is necessary to arrange for sufficient force at the end of the piston stroke to deliver all of the medicament at the required pressure: if a spring is used, this is called "pre-loading".

There is a need to deliver different volumes of medicament according to a patient's age, weight, and factors relating to the condition being treated, and some single use injectors, such as that disclosed in U.S. Pat. No. 4,913,699 (Parsons), may be capable of delivering different volumes because the user must first fill the injector by using a co-operating medicament transfer device, by which means medicament is transferred from a bulk storage vial into the injection cartridge. Thus the user is able to vary the fill volume and hence the dispensed volume. However these injectors, whilst superficially simple, require the use of the transfer device, which is complicated and difficult to sterilise, and the aseptic transfer of medicament is almost impossible to achieve routinely. Furthermore, to the present inventors' knowledge, no prior art single use injectors are known which have an actuator mechanism for varying the energy release to suit the amount to be dispensed.

There are more complex re-usable injectors such, as those sold by the MediJect Corporation, in which the actuator may be adjusted to vary the energy release, but these too suffer most of the same fundamental problems as Parson's injector.

One preferred embodiment in WO 95/03844 is a coil spring powered injector having adjustments for the delivered volume, but even this improvement over the prior art is somewhat complicated to manufacture and operate. Other embodiments in that application describe gas spring powered actuators. (A gas spring comprises a cylinder and piston, with pressurised gas urging the piston which is temporarily restrained by a latch mechanism). A gas spring has several advantages over a coiled spring: in particular, a much higher energy storage density is possible, and at the end of the piston stroke, residual gas may be easily released through an opening in the cylinder wall. This latter point is important to ensure the safe disposal of the injector after use. In the case of a coiled spring-powered actuator, it would require a complicated mechanism to automatically unload the residual energy stored in the spring at the end of its stroke.

Whilst needleless injectors have great potential in reducing pain and fear of needles, and in reducing cross-infection, their high cost compared with a conventional syringe has mitigated against their widespread use, and this is particularly so in relation to injectors which are required to deliver a variable dose.

According to the present invention there is provided an actuator for a gas-powered needleless injector, comprising a drive member movable through a stroke to cause a substance to be delivered by the injector; means for creating a gas pressure on the drive member to cause it to move through the stroke; means for venting the gas pressure after the drive member has travelled through its stroke; and means for adjusting the effective location of the venting means, thereby to adjust the stroke.

A particularly preferred embodiment is an actuator employing a gas spring, as described above, but having a stroke which is easily adjustable in small increments. This is achieved by having a series of valves along the cylinder, so that by opening a particular valve, the pressurised gas driving the piston escapes rapidly through the valve, causing the piston to stop. Although the piston will have some momenturm, in a damped system, which a needleless injector is, the damping and friction will reduce any overtravel to insignificant proportions.

In a first embodiment, a cylinder closed at one end contains a piston which seals and slides against the internal surface of the cylinder. Pressurised gas is contained between the closed end of the cylinder and the piston and urges the piston towards the open end of the cylinder. The piston is temporarily restrained from moving by a latch, operable by a cooperating sliding trigger sleeve. A series of holes aligned longitudinally in the wall of the cylinder between the sealing part of the piston and the open end of the cylinder are covered and sealed by a sleeve slidable over the outside of the cylinder. By moving the sleeve longitudinally the holes may be progressively uncovered, so that when the latch is operated to release the piston, the piston travels in the cylinder bore towards the open end, until the sealing part of the piston passes an uncovered hole, whereupon the pressurised gas escapes rapidly through the hole, and the piston quickly stops. The sliding sleeve has a ratchet or detent to enable the user to preset the sleeve accurately prior to firing the actuator.

In a second embodiment, there is provided an actuator comprising a piston and cylinder as previously described, but having the sliding sleeve movable helically along the outside of the cylinder. In this embodiment the holes through the cylinder wall may also be placed on a helical centreline, so that smaller increments of adjustment are possible.

In yet other embodiments, the piston is connected to a venting member, preferably a rod, which has a vent formed therein, the position of the rod with respect to the piston being variable to adjust the stroke of the piston.

In all embodiments it is desirable that the position of the adjusting means is identified to enable the user to preset the dose.

The effect of shortening the stroke of the piston is to reduce the volume of medicament dispensed from the medicament cartridge, because the piston within the medicament cartridge will also have its stroke reduced. Thus there will be some medicament remaining in the cartridge at the end of the injection. For most medicaments this is unimportant, and in any case, pharmaceutical vials usually contain an excess of the drug required.

Although a gas spring is preferred it is alternatively possible for the gas pressure to be created by a container of gas or vaporisable liquid arranged to apply gas pressure to the drive member upon operation of the actuator.

Details of preferred embodiments of the invention will now be described with reference to the following drawings.

Figure 1:
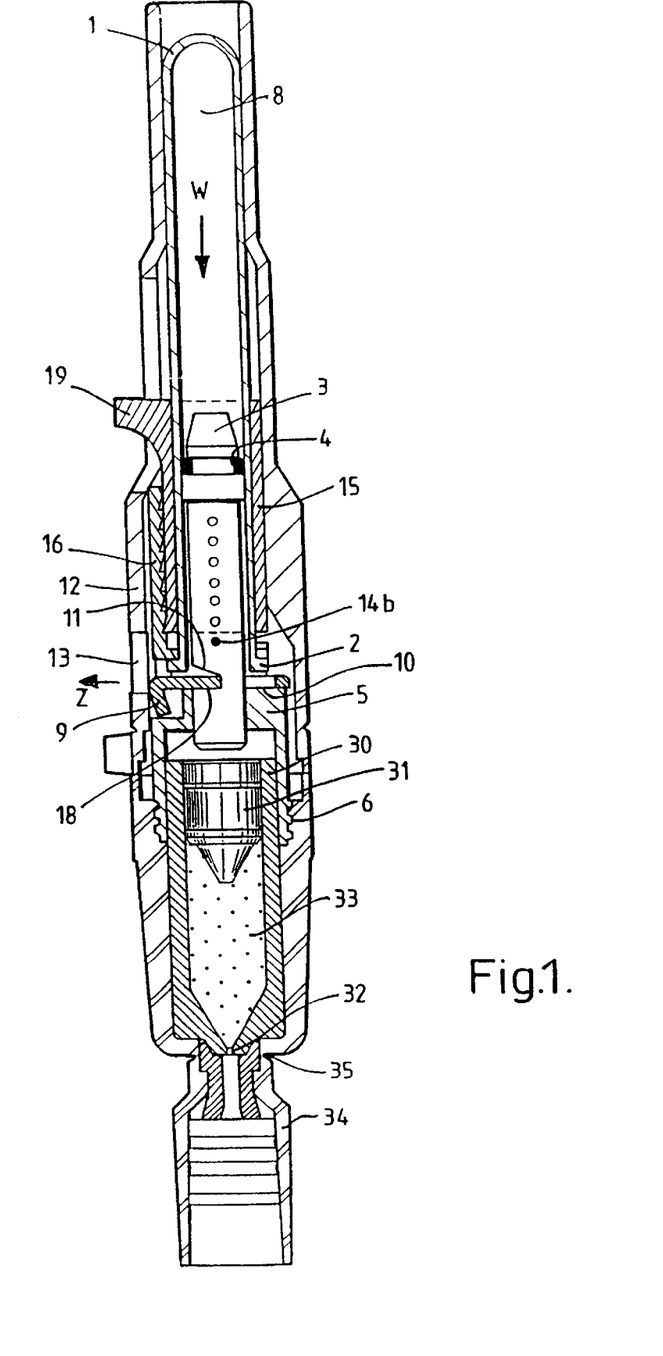
FIG. 1 shows a longitudinal section through a first embodiment of a gas-powered actuator for a needleless injector, employing a longitudinally sliding sleeve for adjusting the piston stroke. (Attention is drawn to International Patent Publication No. WO 97/37705 and its corresponding U.S. Pat. No. 6,135,979, issued Oct. 24, 2000, which is incorporated herein by reference, for a full description of the injector and its operation).
Figure 3:
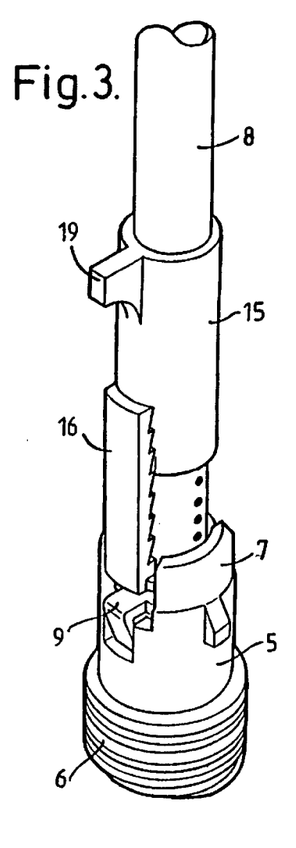

Referring to FIG. 1, the actuator comprises a gas cylinder 1 closed at one end and having an opening at the other end defined by a flange 2. A piston 3 is a sliding fit in the cylinder 1, and carries a seal 4 in sliding contact with the internal cylinder wall. Referring also to FIG. 3, the actuator may be provided with a coupling 5, having a screwthread 6, for connecting it to a medicament cartridge 30 having a cooperating screwthread. The cartridge has piston 31 slidably received therein, and an outlet orifice 32, and between the piston 31 and orifice 32 it is filled with a substance 33 to be delivered by the injector, e.g. a medicament in liquid form. The lower end of the cartridge is sealed by a member 34 which can be broken off at a frangible connection 35 prior to use.

One or more lugs 7 are crimped onto the flange 2 of gas cylinder 1 to retain it. Between its closed end and the seal 4 the gas cylinder is filled with pressurised gas or a mixture of pressurised gas and liquid vaporisable to provide further pressurised gas. This urges the piston 3 in the direction of arrow W. The piston 3 is temporarily restrained by a latch 9 which reacts against a support face 10 on a coupling 5. The latch 9 engages with a cam face 11 in piston 3, so that the force on the piston in the direction of arrow W produces a side thrust on latch 9 in the direction of arrow Z. This has the effect of trying to disengage the latch 9 from the piston 3, thus firing the actuator, but this action is prevented by the inner wall of an operating sleeve 12. When the operating sleeve 12 is moved in the direction of arrow W relative to the assembly of gas cylinder 1 and coupling 5, an aperture 13 in the wall of operating sleeve 12 becomes juxtaposed with the latch 9, permitting the latch 9 to disengage from the piston 3. This is the principle of operation more fully described in International Patent Publication No. WO 97/37705, incorporated herein by reference, but it is alternatively possible to employ other triggering mechanisms designed for a specific application. After disengagement of the latch, the piston 3 strikes the piston 31, causing the latter to dispense a dose of the substance 33 through the orifice 32.

Figure 2:
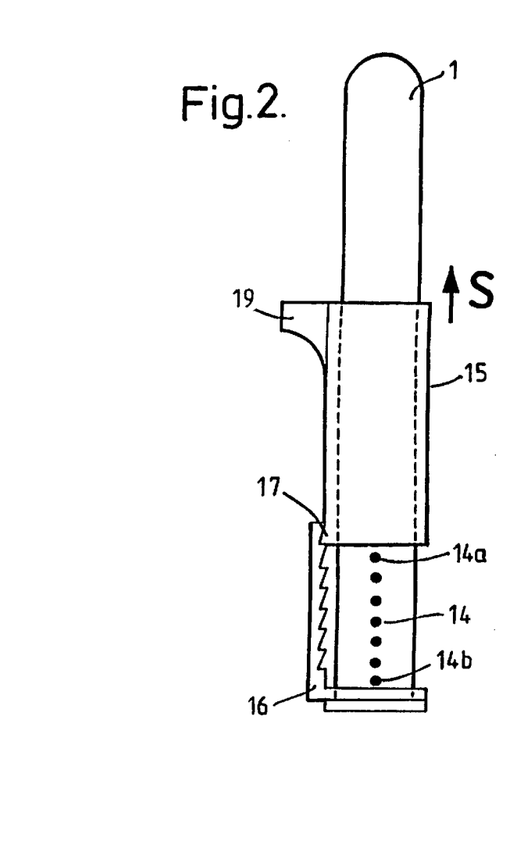
FIGS. 2 and 3 are details of a ratchet co-operating with the sliding sleeve, used in the first embodiment.

Referring particularly to FIG. 2, the cylinder 1 has a series of vent holes 14 located in a longitudinally extending row and perforating the wall of cylinder 1. (The positions of the holes are also indicated in FIG. 1, but it must be understood that the holes are in the cylinder 1 not, as might be thought from FIG. 1, in the piston 3.) A valve sleeve 15 is slidable along the outside of cylinder 1, and also makes reasonable sealing contact with the holes. A pawl 17 on the lower end of the valve sleeve 15 engages with a ratchet 16 which is crimped together with the cylinder 1 by lugs 7 on coupling 5. Thus, by sliding the valve sleeve 15 in the direction of arrow S relative to the assembly of cylinder 1 and coupling 5, the valve sleeve 15 may be moved incrementally to increase the number of holes 14 in the wall of the gas cylinder 1 which are uncovered, but not vice versa. Of course, if a one-way adjustment is not required, then the toothform of the ratchet 16 and pawl 17 may be changed to provide a detent function only.

The topmost hole 14a in the wall of the cylinder 1 may be used for filling the cylinder 1 with compressed gas. The piston is first located in the cylinder 1 so that the seal 4 is just below the hole 14a (below as in the orientation of the drawings), and the pressurised gas 8 is introduced through the hole 14a in the space between the seal 4 and the closed end of the cylinder 1. The piston 3 is pushed fturther into the cylinder 1 until the latch 9 can engage in the slot 18 in the piston 3. With the ratchet disengaged by a suitable tool, the valve sleeve 15 is then pushed to the position shown in FIG. 1 so that all the holes 14 are sealed except for hole 14b.

Figure 4:
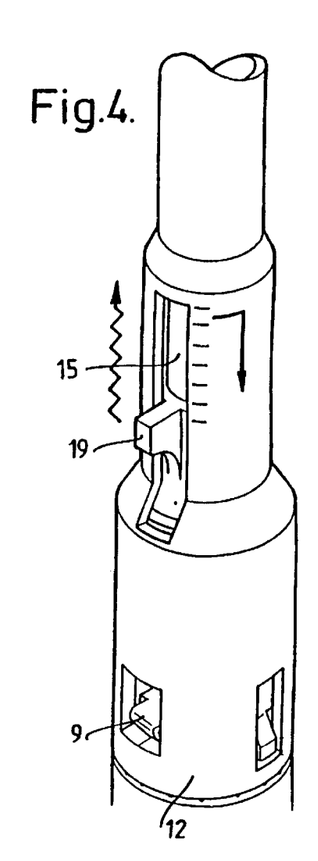
FIG. 4 shows part of the exterior of the first embodiment including a dose indicator
Figure 5:
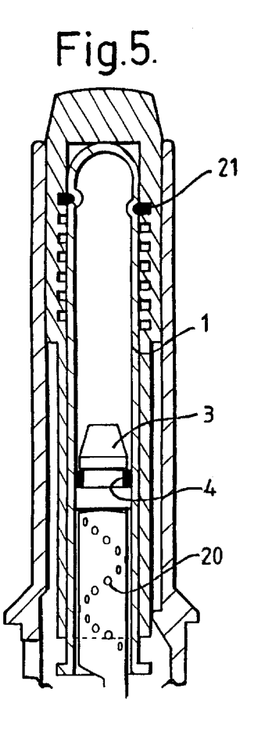
FIG. 5 is a longitudinal section through part of a second embodiment, before firing, having rotary means for adjusting the dose.
Figure 6:
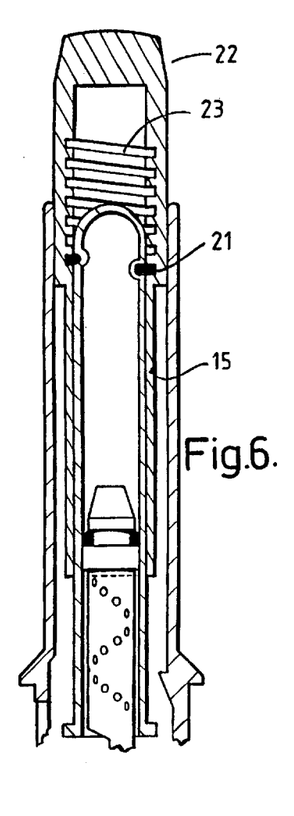
FIG. 6 shows the actuator of FIG. 5 after firing.
Figure 7:
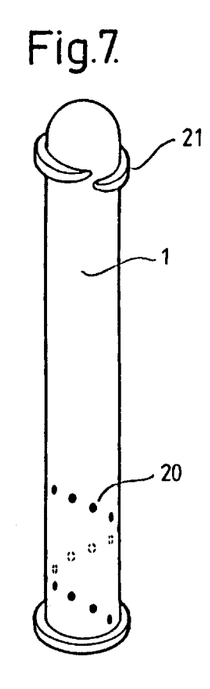
FIG. 7 shows a gas cylinder forming part of the second embodiment, with a helical thread for engagement with an adjustnent knob.
Figure 8:
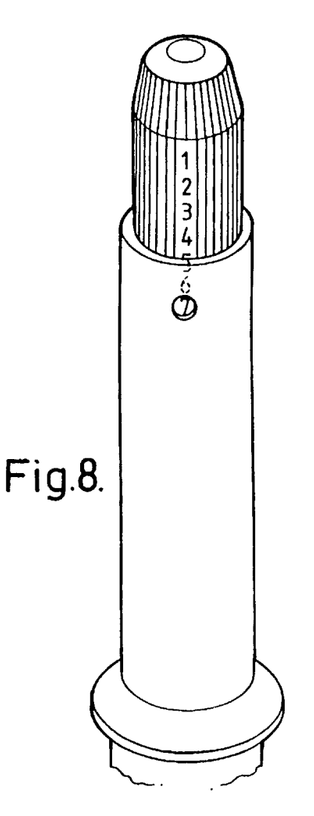
FIG. 8 is a perspective view of the second embodiment, showing particularly the adjustment knob and dose marking.

If the user then operates the actuator by acting on operating sleeve 12, at the end of the piston stroke the seal 4 passes hole 14b, and the residual pressurised gas 8 escapes through the hole 14b. If, however, the sleeve has previously been adjusted to some intermediate position, then when the seal 4 passes the topmost hole uncovered, the gas 8 will escape through that hole and the piston 3 will stop. FIG. 4 shows the exterior of part of the actuator, and illustrates how the valve sleeve 15 may have an operating knob 19 which may also serve as a dose indicator against markings on the outside of the operating sleeve 12.

FIGS. 5–8 show an actuator of similar construction but having rotary means to vary the stroke. In this embodiment, holes 20 are arranged in a helix to give smaller increments of stroke adjustments (but could be arranged linearly as in the first embodiment). Valve sleeve 15 terminates in a knob 22, and the inside of the sleeve 15 has a female screw thread, which cooperates with a male screw thread 21 on the gas cylinder 1. Screw thread 21 may be a separate part which is swaged or crimped on to the cylinder 1. The rotary motion of valve sleeve 15 is translated to linear movement and progressively uncovers the holes 20. When the actuator is operated, the stroke of the piston 3 is terminated at the uppermost uncovered hole 20 when the gas escapes through the said hole.

Figure 9:
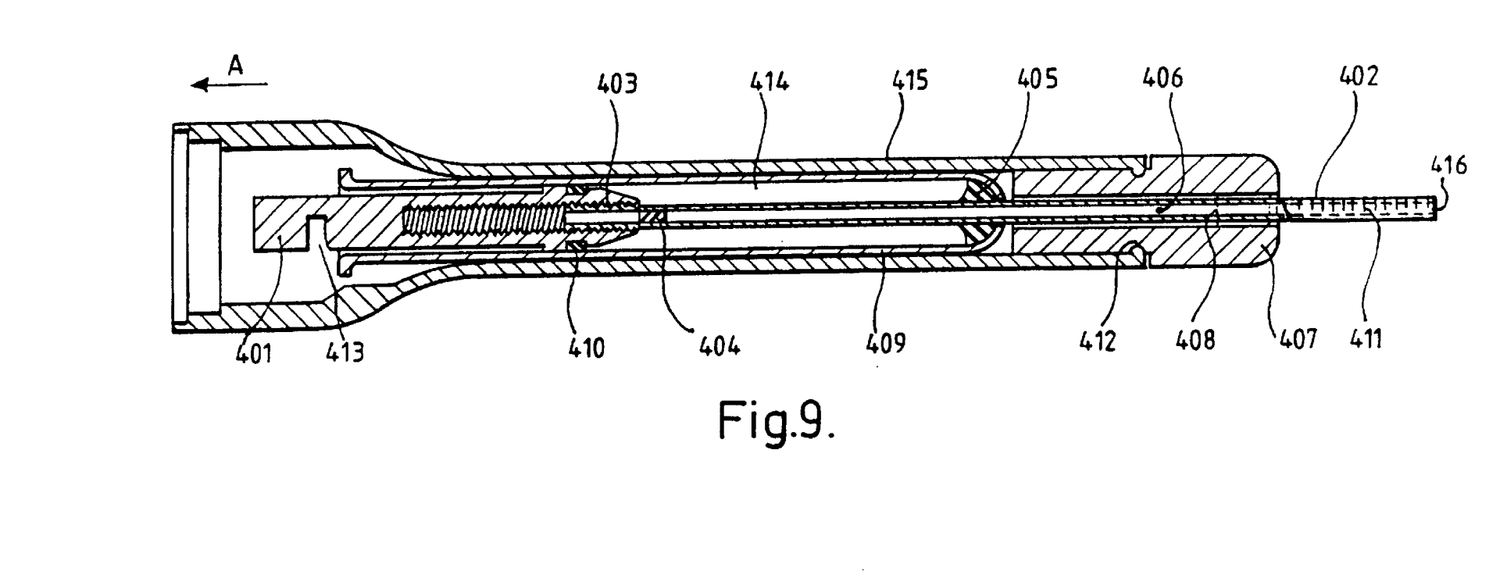
FIGS. 9 to 11 show a third embodiment, with FIGS. 9 and 10 showing the actuator adjusted for two different doses, before firing, and FIG. 11 showing the actuator after firing.

A third embodiment of the invention will now be described with reference to FIGS. 9 to 11. Referring first to FIG. 9, a ram 401 is attached by screw threads 403 to a hollow adjusting rod 402, and the ram and rod are assembled into a gas cylinder 409. The cylinder 409 contains a pressurised gas 414, such as nitrogen, or a mixture of pressurised gas and vaporisable liquid, which is prevented from escaping by a ram seal 410 and a rod seal 405, the latter being sealingly attached to the gas cylinder 409. The assembly of the ram 401, seal 410, and rod 402 is free to slide longitudinally in the bore of the cylinder 409, and therefore the pressurised gas urges the ram 401 in the direction of arrow A. The ram is temporarily prevented from movement by a latch (not shown) engaged in a slot 413, operable by a trigger release mechanism configured to suit the application (not shown).

The rod 402 is hollow, and has a plug 404 sealingly assembled therein to prevent the escape of the pressurised gas 414 through the hollow rod 402 via the threads 403. A hole 406 perforates the wall of the hollow adjusting rod 402, and the bore of the hollow adjusting rod 402 is open to the atmosphere at 416. The assembly of the cylinder 409 and ram 402 is housed within the sleeve 415. An adjustment knob 407 is free to rotate on the end of the sleeve 415, and is retained thereon by a detent 412. Part of the rod 402 is deformed to form a key 408 which is free to slide within a cooperating groove in the knob 407. Thus, when the knob 407 is rotated, the rod 402 is rotated with it, and the rod 402 will be screwed into or out of the ram 401. The ram is prevented from rotating with the rod 402 by the trigger latch or other location means, or alternatively the friction of the seal 410 on the bore of cylinder 409 may be sufficient to prevent rotation.

Figure 10:
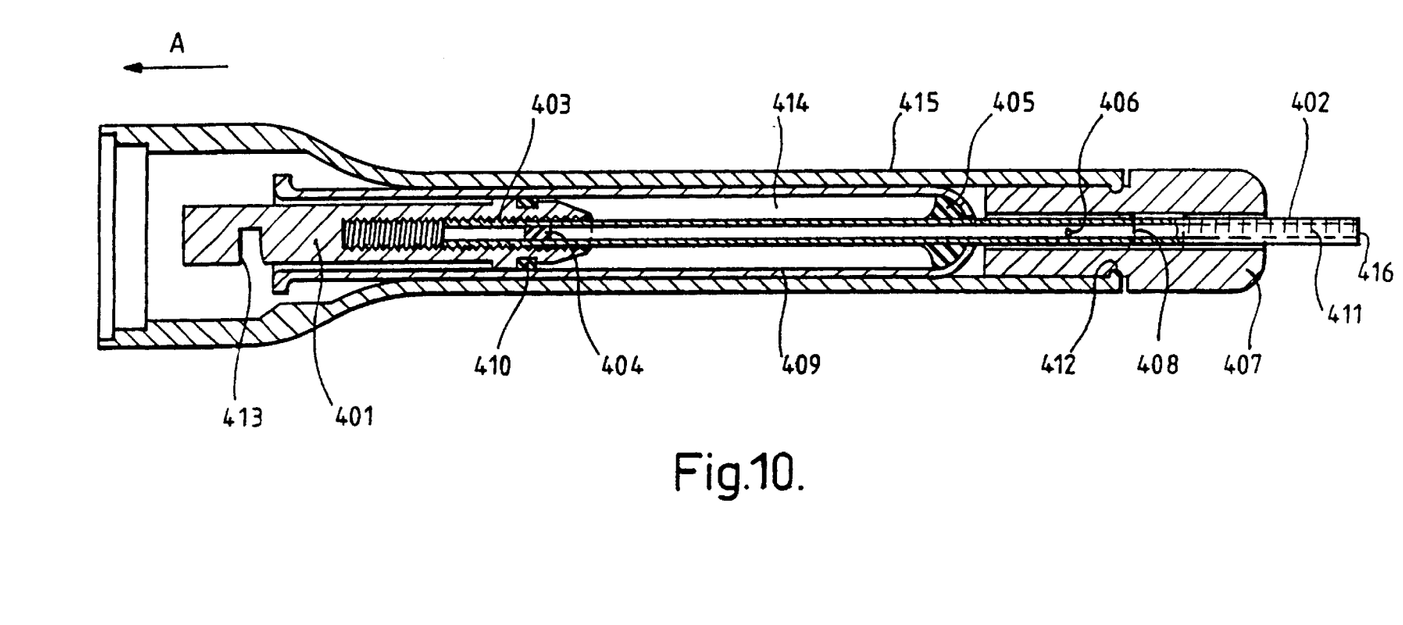

Referring to FIG. 10, the effect of rotating the adjustment knob 407 may be seen, i.e. the rod 402 is screwed further into the ram 401, and the hole 406 is closer to the seal 405. The stroke of the ram is indicated by the position of the graduations 411 relative to the end face of the adjusting knob 407.

Figure 11:
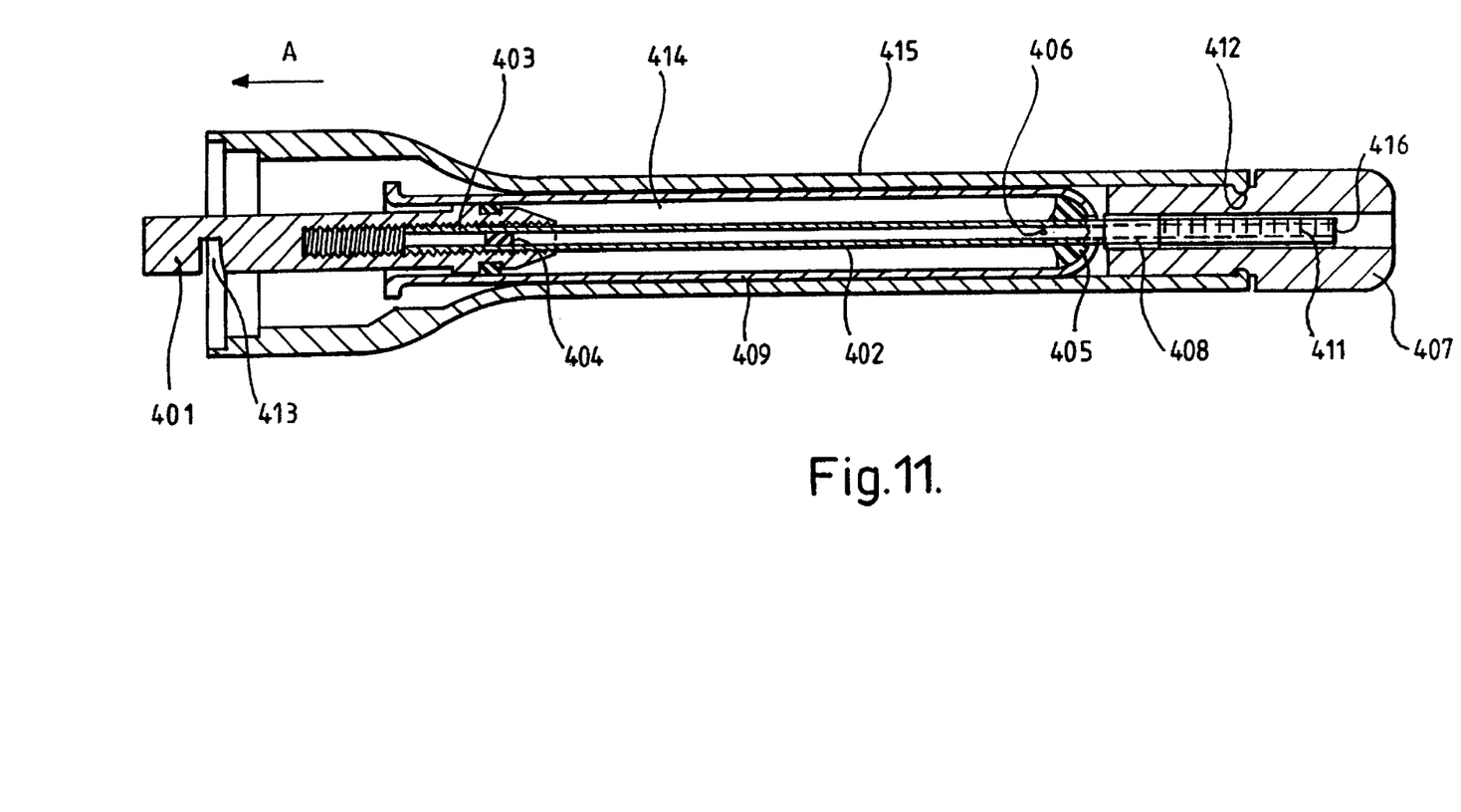

Referring to FIG. 11, the latch has been disengaged from the trigger slot 413 in the ram 401, allowing the pressurised gas 414 to move the ram and rod assembly in the direction of arrow A. When the hole 406 passes through the seal 405, it enters the inside of the cylinder 409 and allows the pressurised gas to escape via the bore of the hollow adjusting rod and to atmosphere through the open end at 416. Since there is now no motive force available from the gas, the ram stops almost immediately, dependent on the flow rate of the pressurised gas through the hole 406 and bore of the hollow rod 402. Thus, by adjusting the position of the hole 406 relative to the seal 405, the stroke of the ram and hollow rod assembly may be varied.

Figure 12:
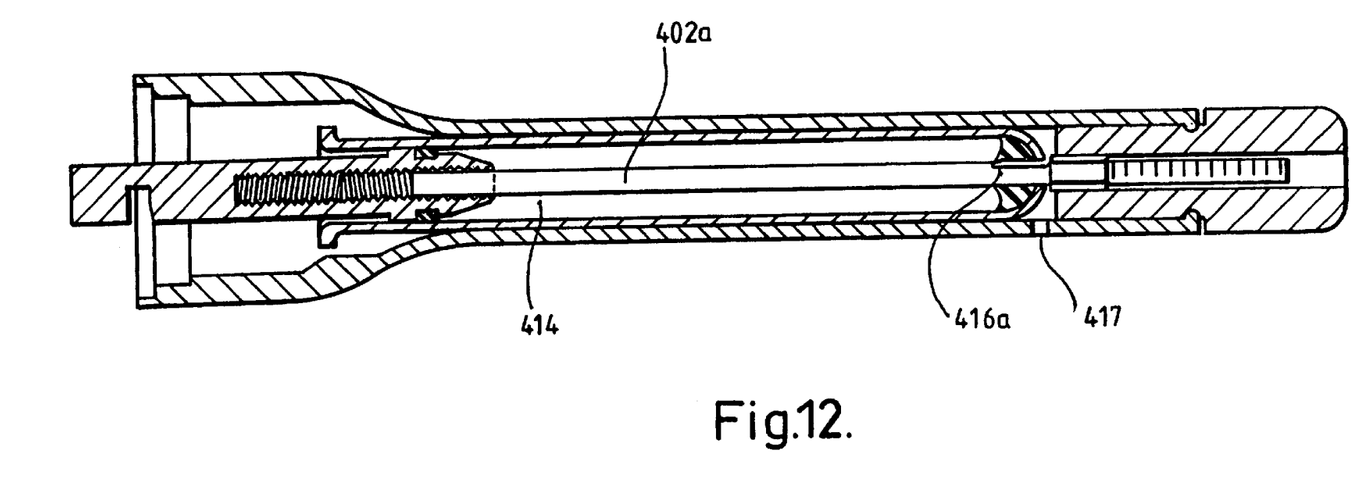
FIG. 12 shows a fourth embodiment, after firing.

FIG. 12 shows a fourth embodiment in an operated position corresponding to FIG. 11 for the third embodiment. The fourth embodiment is similar to the third, but in this case a solid rod 402a replaces the hollow rod previously described, and the hole 406 is replaced by a bypass groove or flat 416a. When the rod 402a is in the position shown, the pressurised gas 414 escapes through the bypass groove 416a to atmosphere via vent 417.

The foregoing examples show that the addition of very few components to a simple gas powered actuator can provide stroke adjustment together with safe escape of residual pressurised gas at the end of actuation.

What is claimed is:

1. An actuator for a gas-powered needleless injector, comprising a drive member movable through a stroke to cause a substance to be delivered by the injector; means for creating a gas pressure on the drive member to cause it to move through the stroke; means for venting the gas pressure after the drive member has travelled through its stroke; and means for adjusting the effective location of the venting means, thereby to adjust the stroke, said venting means comprising a plurality of vent openings arranged at different distances along the stroke, and the adjusting means comprising a member for determining which of the vent openings is the effective venting means.

2. An actuator according to claim 1, wherein the said member of the adjusting means is a sleeve movable to selectively seal or expose given vent openings.

3. An actuator according to claim 2, wherein the vent openings are arranged in a line parallel to the direction of movement of the drive member.

4. An actuator according to claim 2, wherein the vent openings are arranged along a helical line.

5. An actuator according to claim 2, wherein a plurality of possible locations for the sleeve are defined by a detent system.

6. An actuator according to claim 2, wherein a plurality of possible locations for the sleeve are defined by a ratchet system, whereby the sleeve is movable in use only in one direction.

7. An actuator according to claim 2, wherein the adjusting means includes a rotatable knob, connected to the sleeve, and the adjusting means further comprises a screwthread system for converting rotational movement of the knob into linear movement of the sleeve.

8. An actuator according to claim 1, wherein the means for creating a gas pressure is a gas cylinder in which the drive member is received for movement during its stroke, a latch arrangement being provided to prevent movement of the drive member prior to operation of the actuator.

9. An actuator according to claim 1, wherein the means for creating a gas pressure is a container of gas or vaporisable liquid arranged to apply gas pressure to the drive member upon operation of the actuator.

10. An actuator according to claim 1, wherein the drive member is arranged to strike a dispensing piston after the drive member has travelled through part of its stroke, and thereafter to cause the dispensing piston to dispense the said substance from the injector, while the drive member completes its stroke.

* * * * *